(12) United States Patent
Konkle et al.

(10) Patent No.: US 10,045,748 B1
(45) Date of Patent: Aug. 14, 2018

(54) X-RAY DETECTOR STRUCTURE

(71) Applicant: General Electric Company, Schenectady, NY (US)

(72) Inventors: Nicholas Konkle, Waukesha, WI (US); Kevin Lee, Waukesha, WI (US); Connor Douglas McColl, Waukesha, WI (US); Kevin Kinsey, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 15/719,999

(22) Filed: Sep. 29, 2017

(51) Int. Cl.
    *A61B 6/00* (2006.01)
(52) U.S. Cl.
    CPC .................. *A61B 6/4283* (2013.01)
(58) Field of Classification Search
    CPC .................. G01T 1/2018; A61B 6/4283
    See application file for complete search history.

(56) References Cited

U.S. PATENT DOCUMENTS

| | | | |
|---|---|---|---|
| 5,804,832 A | 9/1998 | Crowell et al. | |
| 6,025,598 A | 2/2000 | Tago | |
| 6,700,126 B2 | 3/2004 | Watanabe | |
| 6,825,472 B2 | 11/2004 | Endo | |
| 6,897,449 B1 | 5/2005 | Hata | |
| 7,057,181 B2 | 6/2006 | Yagi | |
| 7,189,972 B2 | 3/2007 | Ertel et al. | |
| 7,317,190 B2 | 1/2008 | Ertel et al. | |
| 7,397,037 B2 | 7/2008 | Watanabe | |
| 7,488,946 B2 | 2/2009 | Hennessy et al. | |
| 7,495,226 B2 | 2/2009 | Jadrich et al. | |
| 7,495,227 B2 | 2/2009 | Hennessy et al. | |
| 7,556,877 B2 | 7/2009 | Suda et al. | |
| 7,569,831 B2 | 8/2009 | Jadrich et al. | |
| 7,582,877 B2 | 9/2009 | Dobrusskin et al. | |
| 7,745,797 B1 | 6/2010 | Liu et al. | |
| 7,800,065 B2 | 9/2010 | Konkle et al. | |
| 7,881,436 B2 | 2/2011 | Rogers et al. | |
| 2005/0017188 A1 | 1/2005 | Yagi | |
| 2007/0072445 A1 | 3/2007 | Spahn | |
| 2008/0078940 A1 | 4/2008 | Castleberry et al. | |
| 2009/0122959 A1 | 5/2009 | Jadrich et al. | |
| 2010/0128850 A1 | 5/2010 | Konkle | |
| 2010/0264572 A1 | 10/2010 | Konkle | |
| 2011/0133085 A1 | 6/2011 | Konkle et al. | |

(Continued)

*Primary Examiner* — David Porta
*Assistant Examiner* — Faye Boosalis (57) ABSTRACT

An x-ray detector for obtaining x-ray images of an object is provided that is capable of increasing the ability of the detector to withstand shock and other types of forces acting on the enclosure to prevent and/or limit damage to the internal components of the detector. The enclosure includes an internal filler/force distribution layer formed from a lightweight, rigid material such as rigid foam and/or a suitable structure, such as a honeycomb or other lattice structure. The material is formed or shaped to fill a layer or portion of the interior of the detector that is otherwise empty space defined between the various internal components of the detector. The position and shape of the force distribution layer determines the path of load distribution across or through the enclosure away from the internal components of the detector and is optimized for shock absorption and/or load distribution.

19 Claims, 6 Drawing Sheets

(56) References Cited

U.S. PATENT DOCUMENTS

2011/0133096 A1\* 6/2011 Konkle .................. G01T 1/244
                                                    250/370.09
2015/0164447 A1   6/2015 Couture \* cited by examiner

X-RAY DETECTOR STRUCTURE

BACKGROUND OF INVENTION

In order to obtain X-ray images of interior structures of a body, such as a piece of luggage or the body of a patient, various types of imaging systems are employed. In many prior art imaging systems, the detector is formed as a separable component from the remainder of the imaging system. The detector is formed as a cassette-like structure with a housing enclosing the components of the detector necessary to detect the impingement of X-rays thereon to form the X-ray image.

In many detector structures, the cassette enclosure includes a rigid back cover secured to a front cover off the cassette. The enclosure contains various components for enabling the detector to function as desired, including an imager that is struck by the X-rays, different electronic components for receiving data from the imager, a backscatter shield and a power source for supplying power to the various component of the detector.

The materials utilized to for the components of the detector are rigid in nature in order to provide structural integrity to the detector and to provide a level of protection for the internal components. However, when in use significant stresses are applied to the detector, such as when placing a patient in a standing position on the detector prior to obtaining the x-ray image with the detector and imaging system.

In these situations, stepping on the detector causes the enclosure to deflect which can cause the enclosure and/or components within the enclosure to crack or deform as a result of the deflection and applied pressure. Further, in the event that the detector is dropped, the force of the shock on the impact can also cause damage to the enclosure and/or internal parts of the detector.

In order to addresses these issues with the structure of the detector, prior art detectors include shock mounts disposed within the enclosure between the internal components and the enclosure. The mounts are formed of an elastomeric, rubber or similar material and operate to separate or indirectly connect the internal component with the enclosure at the specific mounting points/points of contact between the enclosure and the internal components. Upon stress or forces being applied to the enclosure, the compressible nature of the material forming the shock mounts enable the internal component to move within and/or shift with respect to the enclosure, e.g., from 2-3 mm, in an attempt to minimize the effects of the force on the internal components.

However, the shock mounts are capable of only directing the forces applied to the enclosure directly through the mounts, without being able to significantly dissipate the effects of the applied force across the enclosure. Further, the inclusions of the shock mounts complicate the internal structure of the detector where space is at a premium. Also, the shock mounts do not address the effects of the force on the enclosure, and thus do not provide a significant benefit to the structure of the detector enclosure.

Accordingly, it is desirable to provide detector for an X-ray imaging system having an enclosure capable of effectively distributing forces applied to the enclosure to protect both the detector enclosure and the internal components of the enclosure.

BRIEF DESCRIPTION OF THE INVENTION

There is a need or desire for an enclosure for an x-ray detector that is capable of increasing the ability of the detector to withstand shock and other types of forces acting on the enclosure to prevent and/or limit damage to the internal components of the detector. The enclosure includes an internal filler/force distribution layer formed from a lightweight, rigid material such as rigid foam having suitable structure, such as a honeycomb or other lattice structure. The material is formed or shaped to fill a layer or portion of the interior of the detector that is otherwise empty space defined between the various internal components of the detector. The position and shape of the force distribution layer determines the path of load distribution across or through the enclosure away from the internal components of the detector and is optimized for shock absorption and/or load distribution.

The force distribution layer acts as a load distributor, shock absorber, and/or chassis within the enclosure. The force distribution layer includes cutouts or pockets corresponding to the position of various internal components of the detector, such as batteries, and/or smaller cutouts surrounding groups of components located on the circuit boards disposed within the enclosure for the detector. The positioning of the force distribution layer enables a load or other force exerted on the enclosure to be distributed more evenly through the detector without putting stress on sensitive components or through the circuit boards without stressing the components of the circuit boards. For example, in the event of an individual steps onto the detector including the force distribution layer, the load is distributed via the force distribution layer through the enclosure from the front surface to the back surface. Additionally, as a result of this force distribution capability, an enclosure including the force distribution layer can eliminate the need for separate shock mountings, and/or structural support ribs on the enclosure. Further thinning of enclosure materials can also be made possible, since the planar stiffness of the enclosure front and back face are less essential.

According to a further exemplary aspect of the invention, an x-ray detector includes an enclosure, an imager disposed within the enclosure, an electronics layer disposed within the enclosure and operably connected to the imager and at least one filler layer disposed within the enclosure and between the electronic layer and the enclosure.

According to still a further aspect of the invention, a method for forming a detector for use in conjunction with an X-ray imaging system includes the steps of forming at least one filler layer of a high compressive strength, low density material, the at least one filler layer including a number of apertures extending at least partially through the at least one filler layer therein and positioning the at least one filler layer within an enclosure for the detector between an electronics layer and the enclosure in order to distribute forces acting on the detector through the detector.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
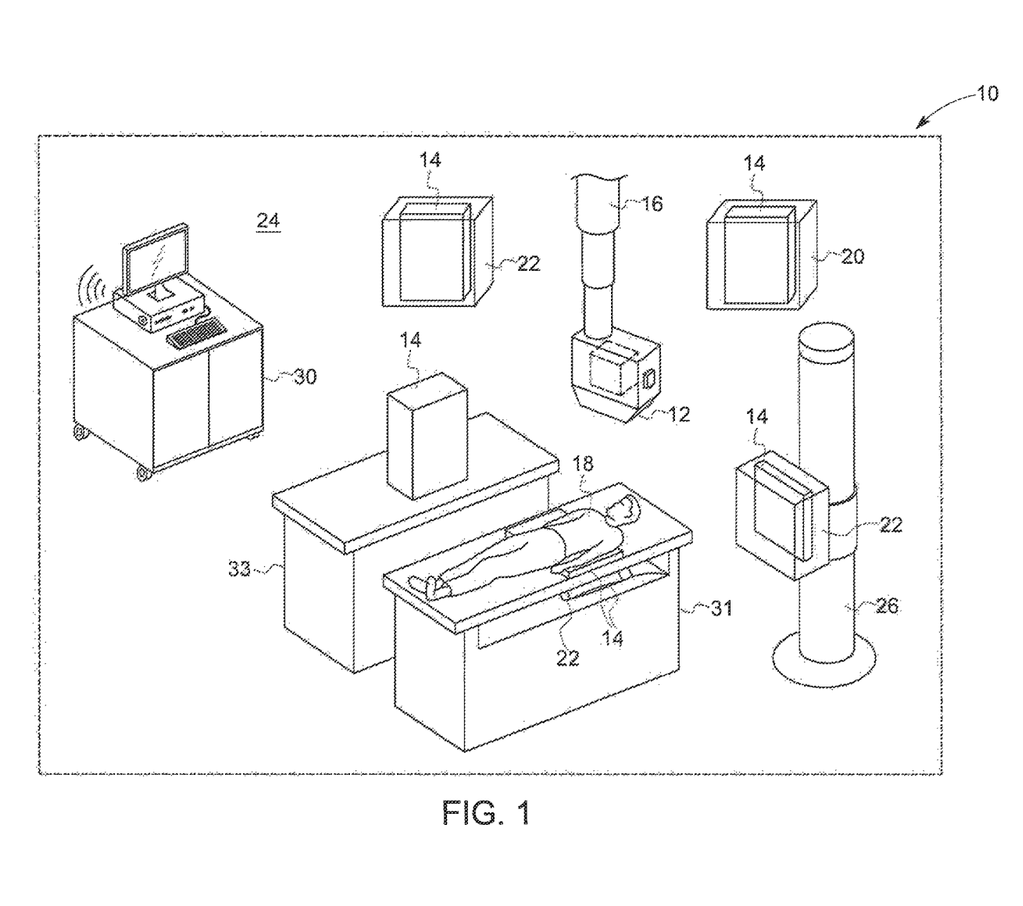
FIG. 1 is a pictorial view of a medical imaging system formed according to an exemplary non-limiting embodiment of the invention.

FIG. 1 is a pictorial view of an exemplary imaging system 10 formed in accordance with an embodiment of the present invention. Various embodiments of the invention may be used with the exemplary medical imaging system 10 as shown in FIG. 1. The medical imaging system 10 may be any type imaging system such as, for example, an x-ray imaging system or a tomosynthesis imaging system. Moreover, the various embodiments are not limited to medical imaging systems for imaging human subjects, but may include veterinary or non-medical systems for imaging non-human objects, or non-destructive testing systems (e.g. airport baggage systems) etc.

Figure 2:
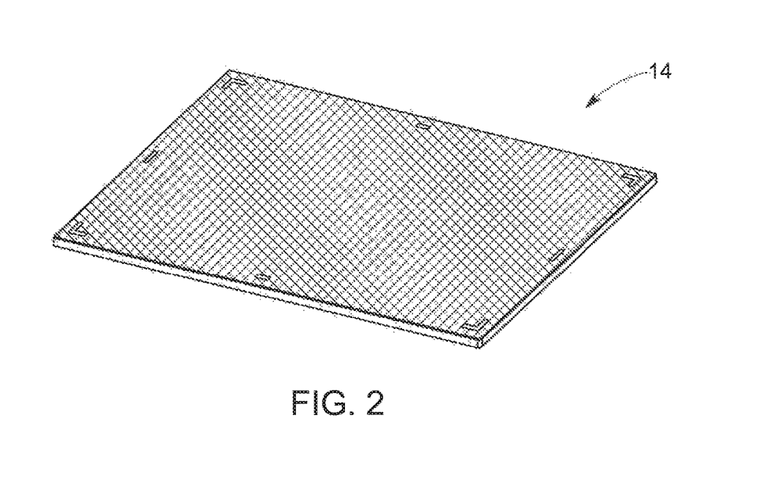
FIG. 2 is an isometric view of an x-ray ray detector cassette/enclosure according to an exemplary non-limiting embodiment of the invention.

The medical imaging system 10 in the preferred embodiment is a digital radiography imaging system 10 that includes an x-ray source 12 and at least one detector 14. In the exemplary embodiment, the detector 14 is a portable x-ray detector. As shown in FIG. 2, the detector 14 may be utilized in various locations and applications, and in either a fixed state or a portable state. The x-ray source 12 is mounted to a gantry 16. The gantry 16 may be movable to enable the x-ray source 12 to be properly positioned with respect to a subject 18 being imaged or to enable the x-ray source 12 to be moved from one imaging room to another. Optionally, the gantry 16 may be mounted to a floor or ceiling, for example.

When the cassette holder 22 is coupled to the wall 24 or the post 26, the cassette holder 22 is often referred to as a wall bucky. Moreover, the cassette holder 22 may fixedly installed in an imaging table 31. When installed in the imaging table 31, the cassette holder 22 may be referred to as a table bucky. In the fixed state, the detector 14 receives power from the cassette holder 22.

The cassette holder or bucky 22 also enables the x-ray detector to communicate with an imaging workstation, such as an imaging workstation 30. During operation, information is transmitted from the workstation 30 to the detector 14 via wires (such as an Ethernet cable) in the cassette holder 22. Additionally, information generated by the detector 14 may be transmitted to the workstation 30 via wires (such as an Ethernet cable) in the cassette holder 22. The information that is generated and transferred may be at a rate higher than a wireless connection can support. Accordingly, in the fixed state, the detector 14 is mounted in a fixed position to the cassette holder 22 and power and communication signals are transmitted from, and received by the detector 14 via the cassette holder 22.

In another mode of operation, the detector 14 is operated in the portable state. For example, in the portable state, the detector 14 is installed into a charging bin 20. The charging bin 20 is configured to provide power to the detector 14 to charge a battery (not shown) installed in the detector 14, but does not provide a wired communication path between the detector 14 and the imaging workstation 30. In another portable state, the detector 14 receives operational power from the battery installed in the detector 14. This portable state is also referred to herein as digital cassette mode. Additionally, operational and communication signals are transmitted wirelessly between the detector 14 and the workstation 30. For example, as shown in FIG. 1, in the portable state, the detector 14 may be positioned on a table 31 beneath the subject 18. The detector 14 may also be positioned on a separate table 33 that is adjacent to the subject 18. Accordingly, in the portable state, the detector 14 is not coupled to the cassette holder 22.

Figure 3:
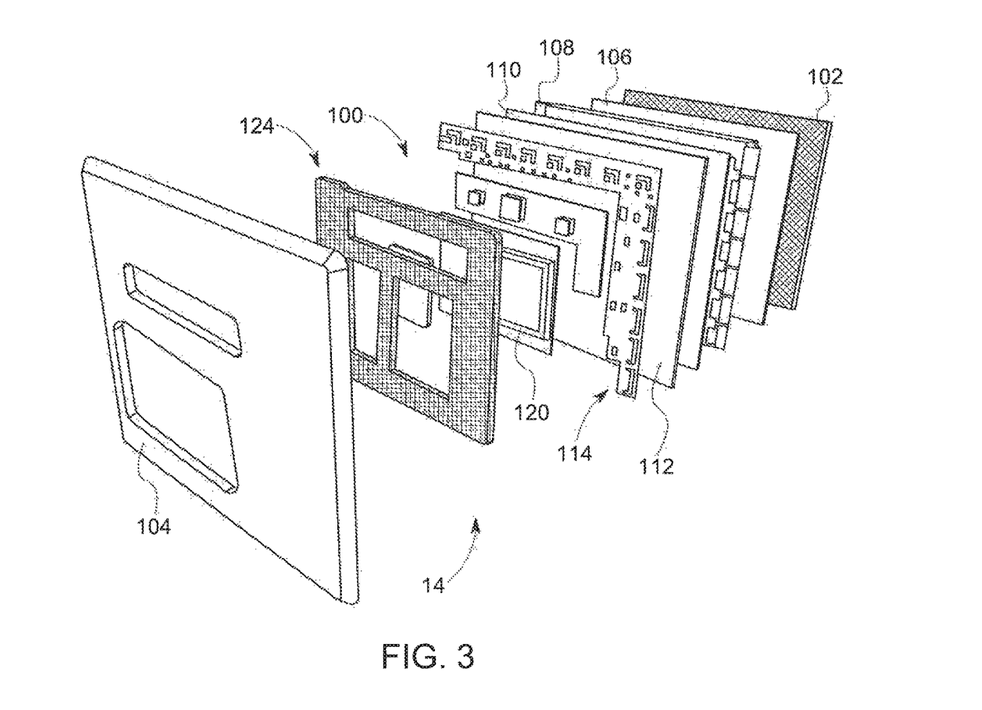
FIG. 3 is an exploded view of the detector cassette/enclosure of FIG. 2.

Looking now at the exemplary illustrated embodiment shown in FIGS. 2 and 3, the detector 14 includes a housing 100 formed with a front cover 102 and a rear cover 104. The front cover 102 and rear cover 104 are normally formed of a rigid and lightweight material on order to provide protection to the interior components of the detector 14 without significantly increasing the weight of the detector 14. In an exemplary embodiment, the front cover 102 is formed of a material that is transparent to x-rays, such as a carbon fiber material, while the rear cover 104 is formed from a metal, such as a lightweight magnesium alloy material.

Between the front cover 102 and rear cover 104 the interior components of the detector 14 include a foam layer 106 disposed immediately adjacent the front cover 102 and present to provide a separation layer between the rigid front cover 102 and an imager 108 disposed adjacent the foam layer 106. The imager 108 is formed in a known manner of a material capable of detecting x-rays striking the imager 108 in order to provide image data concerning the impingements of the x-rays upon the imager 108.

Adjacent the imager 108 but opposite the foam layer 106 is located a lead backscatter shield 110 present to capture any stray x-rays passing through or around the imager 108. The backscatter shield 110 is disposed on one side of a support layer 112. The support layer 112 provides internal structural support to the detector 104 and can be formed of a lightweight and rigid material, such as a magnesium alloy.

Opposite the shield 110, the support layer 112 provides an attachment point for the electronics 114 that are operably connected to the imager 108 and that control the operation of the detector 104. The electronics 114 can include digital electronics 116 and/or scan/data processing electronics 118 that are operably connected to the imager 108 and to one another, as well as to batteries 120 also disposed on the support layer 112. The rear cover 104 is secured to the front cover 102 and the support layer 112 adjacent the electronics 114 in order to provide a rigid enclosure 122 for the various components 106-120 within the detector 14.

Figure 4:
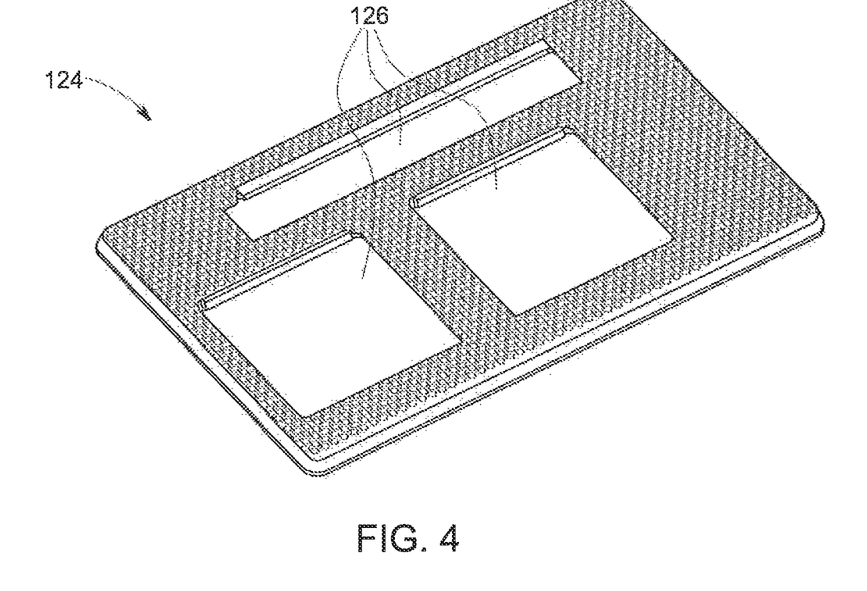
FIG. 4 is an isometric view of a force distribution layer constructed according to an exemplary non-limiting embodiment of the invention.
Figure 5:
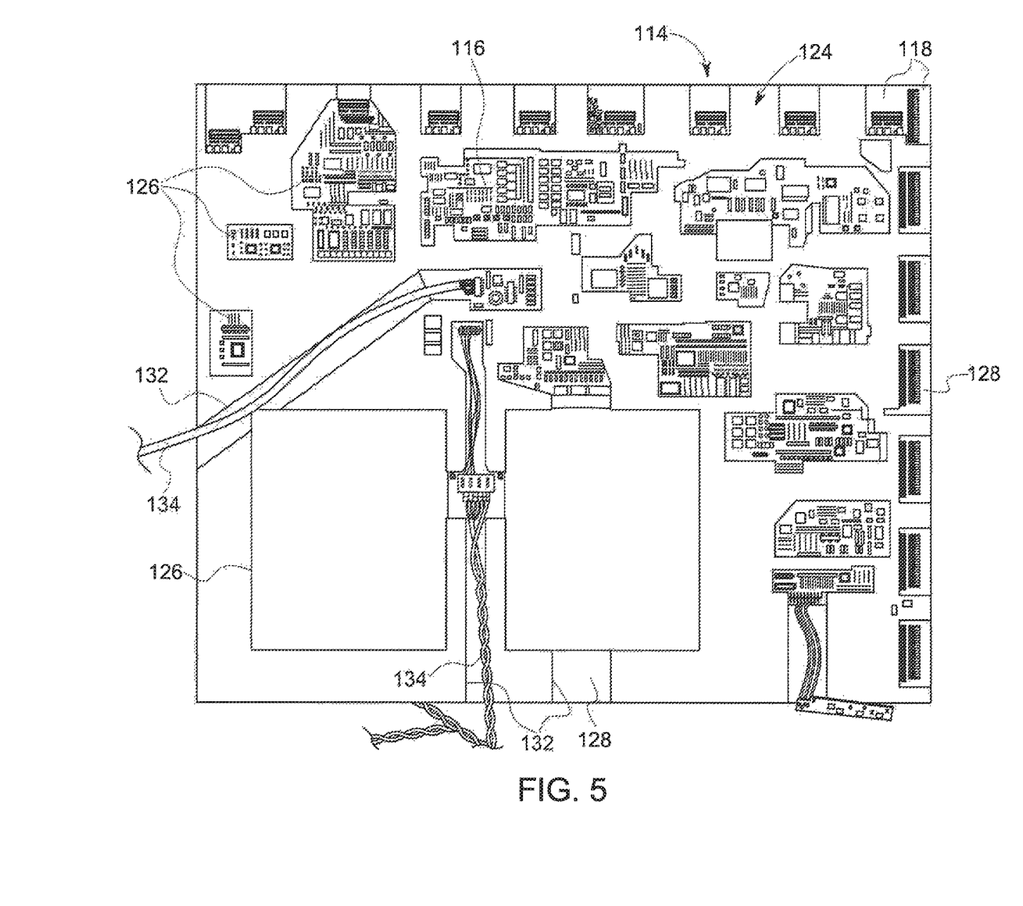
FIG. 5 is a top plan view of a force distribution layer mounted to an electronics layer according to another exemplary non-limiting embodiment of the invention.

Referring now to FIGS. 4-5, between the electronics 114 and the rear cover 104 is disposed a chassis or filler/force distribution layer 124. The force distribution layer 124 is formed to fill the voids present in prior art detectors between the electronics layer 114 and the rear cover 104. The force distribution layer 124 is formed from a material having a high compressive strength and a low density, such that the material is capable of providing significant shock absorption/force transmission properties to the detector 14 but without significantly increasing the overall weight of the detector 14. Exemplary materials for use in forming the filler/force distribution layer 124 include honeycomb materials, foams, gels and rubber-like materials. In one exemplary embodiment, the material forming the filler/force distribution layer 124 is a generally rigid polymeric foam material having a density from 3 to 40 lbs/ft$^3$ with a compressive strength of between 60-250 psi. An example of such a material is are rigid polyurethane foams sold by General Plastics Mfg. Co., of Tacoma, Wash. under the tradename LAST-A-FOAM®.

The filler/force distribution layer 124 is formed with an overall shape corresponding to the shape of the interior of the detector 14 between the electronics 114 and the rear cover 104, and includes apertures 126 corresponding to the shape of the various components on the electronics layer 144, e.g., the digital electronics 116, scan/data electronics 118 and/or batteries 120. In this position, due to the location and the composition of the filler/force distribution layer 124, the layer 124 can transmit and/or distribute any forces acting or exerted upon the detector 14 directly and evenly through the detector 14 from the front cover 102 to the rear cover 104, or vice versa. The location of the filler 124 across the entire interior of the detector 14 enables the filler/force distribution layer 124 to provide contact between the support layer 112 and the rear cover 104 across the entire detector 14. In conjunction with the location of the layer 124, the material forming the filler/force distribution layer 124 enables the filler/force distribution layer 124 can effectively distribute a force on the detector 14 across the entire area of the filler/force distribution layer 124. Additionally, the material forming the layer 124 can also result in a weight reduction through the elimination of the need for any load bearing ribs or shock mounts disposed within the detector 14 and additional thinning of the enclosure 100, and where weight reduction from prior art detector structures of more than 1 kg, and approximately 1.2 kg.

Figure 6:
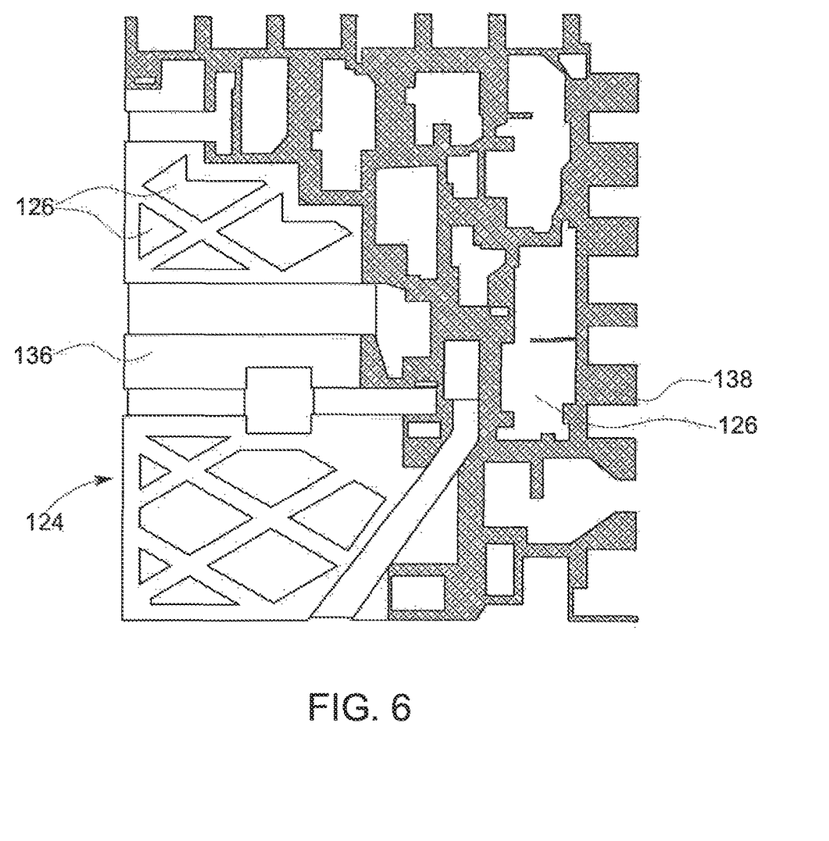
FIG. 6 is a top plan view of a force distribution layer constructed according to another exemplary non-limiting embodiment of the invention.

In the configuration of the filler 124 including the apertures 126, as shown in the exemplary embodiment of FIG. 6, the filler/force distribution layer 124 extends across the entire detector 14 such that a load or force applied to the front cover 102 or rear cover 104 of the detector 14 will be transferred through the filler 124 and around the sensitive components on the electronics layer 114 which will not receive a force from the load. In particular, as shown in FIG. 6 in those areas of the electronics layer 114 formed at least in art with printed circuit boards (PCBs) 128 having individual or groups of sensitive electronic components 130 thereon, such as the digital electronics 116 and/or scan/data electronics 118, the apertures 126 can be formed to closely conform the perimeter of the components 130 on the PCBs 128 in such a way that a force applied on the front cover 102 of the detector 14 is distributed through the filler 124 to the PCB 128 and ultimately to adjacent layers, e.g., the rear cover 104 and/or support layer 112, such that the filler 124 enables the PCB(s) 128, but not the sensitive components 130 disposed on the PCB(s) 128, to function as a portion of a path for bearing load through the detector 14. In addition, the filler 124 can include channels 132 that intersect the perimeter of the filler 124 to allow for wired connections 134 to extend through the filler 124 for connection to the selected components 130.

Figure 7:
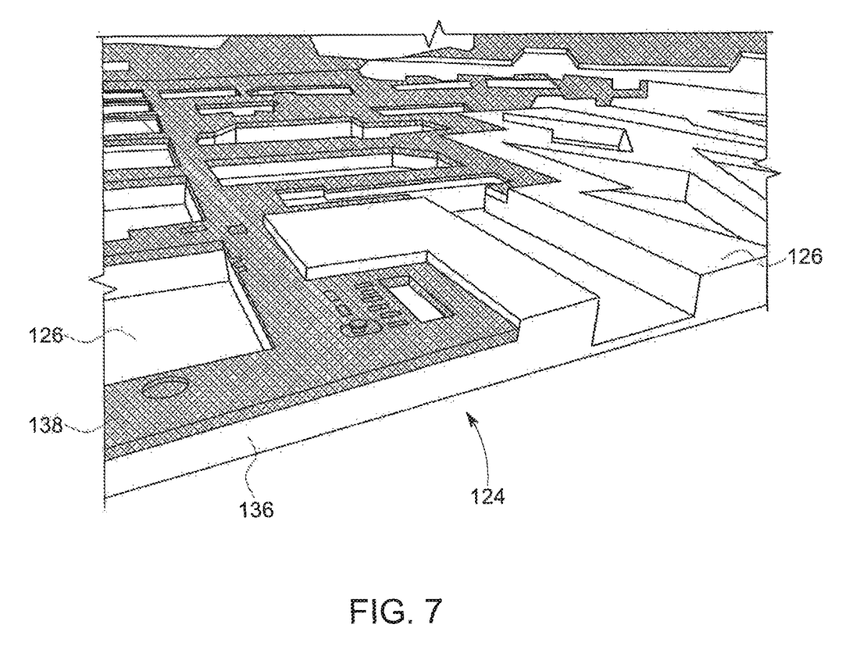
FIG. 7 is a partially broken-away perspective view of the force distribution layer of FIG. 6.

In order to provide the filler/force distribution layer 124 with the desired shape and characteristics, the filler/force distribution layer 124 can be formed in a number of different suitable manners. For example, the material forming the filler 124 can be formed in bulk using any suitable process and subsequently machined or otherwise shaped into the desired configuration. This shaping of the material into the filler 124 can include, for example, laser cutting, machining or rastering the material into the desired shape including the overall shape for placement of the filler 124 within the detector 14 and for the shape of the apertures 126 within the filler/force distribution layer 124. The apertures 126 can be formed to extend completely through the filler/force distribution layer 124, or can be shaped to extend a specified depth or distance into the filler 124 without extending completely through the filler 124. Alternatively, in another exemplary embodiment, the material forming the filler 124 can be shaped by injecting the material directly into the interior of the detector 14 such that the material conforms to the shape(s) of and fills the negative spaces between the particular layers of the detector 14 and around the internal component(s) where the filler 124 is to be positioned In an alternative exemplary structure for and method of forming the filler/force distribution layer 124, the filler 124 may be manufactured with two sheets 136, 138 of similar or dissimilar material forming the filler/force distribution layer 124, as shown in FIGS. 7 and 8. In this exemplary embodiment, the aperture(s) 126 can be formed by cutting, machining, rastering or otherwise shaping the aperture(s) 126 within and/or through one sheet 136 and securing the sheet 136 to the other sheet 138. Further, in exemplary embodiments including one or more layers forming the filler/force distribution layer 124, the filler 124 can be formed in a suitable additive manufacturing process, enabling the materials used in the different portions of the filler 124, and/or the configuration of the apertures 126 to be closely controlled during manufacture of the filler 124.

In addition, in the exemplary embodiment where the filler/force distribution layer 124 includes multiple layers or materials, the filler 124 can be formed with a rigid plastic layer 136 combined with a layer 138 of softer rubber or other cushioning material that is positioned on or against with contact surfaces, such as PCBs 128, within the detector 14. In this exemplary, embodiment, the softer material forming layer 138 can be formed to optimize the shock absorption capability of the filler 124 to allow the filler 124 to function as a shock mount between the points of contact of the layer 138 with other components and/or layers within the detector 14. Further, the filler/force distribution layer 124 can function as a chassis to enable circuit board(s) 128, the rear cover 104, front cover 102, and/or layers of the detector 14 to be mounted directly to the filler 124 in a suitable manner, such as by using any suitable adhesive or mechanical fasteners.

In any of the previously described exemplary embodiments the filler/force distribution layer 124 can be coated or sealed to contain the material forming the filler 124 and avoiding the dissemination of any particles/dust of the material forming the layer 124 within the detector 14, and/or to add other attributes and/or enhancements to the material forming the layer 124, such as anti-static and/or electrostatic property enhancing coatings, or flame retardant coatings, among others.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An x-ray detector comprising:
an enclosure;
an imager disposed within the enclosure;
an electronics layer disposed within the enclosure and operably connected to the imager; and
at least one filler layer disposed within the enclosure and between the electronics layer and the enclosure, wherein the at least one filler layer includes a number of apertures formed therein, the apertures positioned over components of the electronics layer.

2. The detector of claim 1, wherein the at least one filler layer is a material having a high compressive strength and a low density.

3. The detector of claim 2, wherein the material forming the at least one filler layer has a compressive strength of between 60 psi-250 psi.

4. The detector of claim 2, wherein the material forming the at least one filler layer has a density of between 3 lbs/ft$^3$ to 40 lbs/ft$^3$.

5. The detector of claim 2, wherein the material forming the at least one filler layer is a foam material.

6. The detector of claim 1, wherein the electronics layer includes a circuit board on which the components are disposed, and wherein the at least one filler layer contacts the circuit board around the components.

7. The detector of claim 1, wherein the at least one filler layer is formed of multiple materials.

8. The detector of claim 7 further comprising:
a first layer of a first material; and
a second layer of a second material, wherein the second layer is adjacent to the first layer.

9. The detector of claim 8, wherein the first material and the second material have different compressive strength.

10. The detector of claim 8, wherein the first layer at least partially overlays the second layer.

11. The detector of claim 1, wherein the at least one filler layer fills an entire interior space within the enclosure between the electronics layer and the enclosure.

12. An x-ray detector comprising:
an enclosure;
an imager disposed within the enclosure;
an electronics layer disposed within the enclosure and operably connected to the imager; and
at least one filler layer disposed within the enclosure and between the electronics layer and the enclosure, the at least one filler layer comprising a first layer of a first material and a second layer of a second material, the second layer adjacent to the first layer,
wherein at least one of the first layer and the second layer includes a number of apertures therein.

13. The detector of claim 12, wherein one of the first material and the second material is a cushioning material to optimize the shock absorption capability of the at least one filler layer.

14. A method for forming a detector for use in conjunction with an X-ray imaging system, the method comprising:
forming at least one filler layer of a high compressive strength, low density material, the at least one filler layer including a number of apertures extending at least partially through the at least one filler layer therein; and
positioning the at least one filler layer within an enclosure for the detector between an electronics layer and the enclosure in order to distribute forces acting on the detector through the detector.

15. The method of claim 14, wherein the steps of forming the at least one filler layer and positioning the at least one filler layer within the enclosure are performed simultaneously.

16. The method of claim 14, wherein the step of forming the at least one filler layer comprises:
forming a first layer;
forming a second layer; and
placing the first layer and the second layer adjacent to one another.

17. The method of claim 16, wherein the step of first layer and the second layer to one another comprises additively manufacturing the first layer and the second layer.

18. The method of claim 16, wherein the step of positioning the at least one filler layer comprises placing the number of apertures over components disposed on the electronics layer.

19. The method of claim 16 wherein the step of placing the first layer and the second layer adjacent to one another comprises attaching the first layer and the second layer to one another.

* * * * *